(12) United States Patent
Brem

(10) Patent No.: US 7,198,629 B2
(45) Date of Patent: Apr. 3, 2007

(54) MODIFIED EAR TAGS AND METHOD FOR REMOVING TISSUE

(76) Inventor: Gottfried Brem, Thalmannsdorf 25, Larezhausen, 86567 Hilgertshausen (DE)

( * ) Notice: Subject to any disclaimer, the term of this patent is extended or adjusted under 35 U.S.C. 154(b) by 0 days.

(21) Appl. No.: 10/451,975

(22) PCT Filed: Dec. 18, 2001

(86) PCT No.: PCT/EP01/14938

§ 371 (c)(1),
(2), (4) Date: Oct. 30, 2003

(87) PCT Pub. No.: WO02/052928

PCT Pub. Date: Jul. 11, 2002

(65) Prior Publication Data

US 2004/0093775 A1    May 20, 2004

(30) Foreign Application Priority Data

Jan. 1, 2001    (EP)    ................... 01100201

(51) Int. Cl.
*A61B 17/00*    (2006.01)
*A61D 1/04*    (2006.01)

(52) U.S. Cl. ............. 606/116; 600/562; 600/564; 606/117

(58) Field of Classification Search ............... 606/116, 606/117, 131, 139, 188, 562–567; 40/300–302
See application file for complete search history.

(56) References Cited

U.S. PATENT DOCUMENTS

| 4,470,212 A * | 9/1984 | Stafford et al. ............... 40/301 |
| 6,509,187 B2 * | 1/2003 | Brem ...................... 435/288.2 |
| 6,659,338 B1 * | 12/2003 | Dittmann et al. ........... 235/375 |
| 2005/0228310 A1 * | 10/2005 | Pfistershammer ........... 600/567 |

FOREIGN PATENT DOCUMENTS

EP    1 060 662    * 10/2000

* cited by examiner

*Primary Examiner*—Michael J. Hayes
*Assistant Examiner*—Michael G. Mendoza
(74) *Attorney, Agent, or Firm*—Dickinson Wright PLLC; William H. Honaker

(57) ABSTRACT

The invention relates to modified ear tags comprising a mandrel-type plate (10), a counter plate (11), in addition to a container for receiving a sample (1) and a means for obtaining the sample (4). The means for obtaining the sample (4) has a detachable hollow tip and the counter-plate (11) has no through opening for the mandrel. The invention relates more particularly to the use of the ear tags for genotypical analysis of animal populations and to a method for analyzing animal populations with the ear tags.

4 Claims, 4 Drawing Sheets

MODIFIED EAR TAGS AND METHOD FOR REMOVING TISSUE

BACKGROUND OF THE INVENTION

1. Field of the Invention

The invention relates to modified ear tags, comprising a mandrel-type plate, a counter-plate, in addition to a container for receiving a sample and a means for obtaining said sample, wherein the means for obtaining said sample has a detachable hollow tip and the counter-plate has no through opening for the mandrel. The invention relates more particularly to the use of said ear tags for marking animals by simultaneously withdrawing a biological sample, as well as to a method for marking animals with said ear tags.

2. Description of Related Art including information disclosed under 37 CFR 1.97 and 1.98

Ear tags (or ear marks) have been used for a long time for marking and identifying animals, whereby flexible ear tags/ear marks made of plastics, mostly polyurethane or polyethylene, have generally been adopted in the last years. All of said ear tags comprise a mandrel-type plate, also called male part of male flag, and a female part, the counter-plate or female flag. The mandrel-type plate normally comprises a mandrel carrying a tip made of metal or a hard plastics material. The counter-plate comprises an opening, through which the mandrel is pressed when the ear tag is closed after the ear has been penetrated, so that said two ear tag parts are connected with each other. When inserting conventional ear tags, the ear is punctured with the sharp tip of the mandrel, i.e. the tip penetrates through the skin, the cartilage and the skin on the opposite side of the ear.

The tip of the mandrel of the ear tag is normally pushed through the skin and the cartilage in a punctual manner, and the skin and the cartilage are ripped up in the form of a longitudinal tear to an extent sufficient to allow the entire head of the mandrel to slip there through. The result is that the mandrel of the inserted ear tag is more or less firmly surrounded by the spread apart ear tissue which closes elastically. A drawback thereby resides in that the margins of the wound are strongly irritated by the rotational and, drawing movements of the ear tag in the wound so that the healing thereof is inhibited. Present or penetrated bacteria may moreover frequently cause swellings, suppuration with secretion congestion and the development of luxuriant granulation tissue.

Ear tags have lately also been used to simultaneously obtain a tissue sample for a later DNA analysis when the ear tag is inserted. A method for withdrawing a tissue sample into numbered sample capsules is, for example, described in DE 197 40 429 A1. According to this method the numbers of the used ear tags and the numbers of the sample container are linked to each other electronically.

An ear tag is additionally described in PCT/EP98/03075, according to which the ear tag and the receiving container are provided with the same coding and the same animal identification number by means of laser or other technologies prior to the issue to the users. This ensures an identity linking of ear tag and tissue sample receiving container without errors and confusions. The hollow tip of the mandrel, which is connected with the mandrel via a predetermined breaking point, takes a sample in the ear, transports the same automatically into the receiving container, separates from the mandrel and hermetically seals the sample in the receiving container.

The container for receiving the sample is normally withdrawn and collected after the ear tag has been inserted. It may, however, also adhere to the ear tag without any problems and thus remain on the animal, if desired. The processes of inserting the ear tags and obtaining the tissue sample thus take place independently of each other. The collection of the tissue sample may, in principle, even take place years after the ear tag was inserted, by separating at this time only the container for receiving the sample from the female flag of the ear tag.

In the European Union it is stipulated by legal regulation that all born calves have to be provided with two ear tags within the first week after their birth. If the ear tags described in PCT/EP98/03075 are now used for said marking, the receiving container of the one ear tag could, for instance, be withdrawn immediately after the ear tag was inserted, whereas the receiving container of the second ear tag remains—connected with the female flag—on the animal. Later, e.g. when the animal is exported, slaughtered or cut up, the second container for receiving the sample still provided on the animal, which contains a sample since the ear tag was inserted, is withdrawn and delivered to the laboratory for the analysis of the same. This procedure saves, in view of the test sample, the recovery and the marking of a new sample and enables the obtainment of an unmistakable second sample, as the same was marked with the ear tag simultaneously, which had been withdrawn already at the beginning of the animal's life, but was preserved in the container 1 for receiving the sample and remained on the animal and is used, for example, only at the end of the animal's life.

It has shown that it may happen with newborn animals of certain species that the withdrawal of a sample cannot be accomplished with the desired reliability. If animals, especially lambs or piglets, are very young, the entire ear is so soft that its resistance during the punching process is too small. If the insertion of the ear tags is performed in an unskilled manner, the ear tissue is consequently ripped up and not precisely punctured/punched. In such cases a withdrawal/recovery of a tissue sample does not always take place. The function of the ear tag is, as such, not influenced thereby.

It was, therefore, the object of the present invention to overcome the aforementioned drawbacks of the prior art.

BRIEF SUMMARY OF THE INVENTION

Said object was provided by a modified ear tag, comprising a mandrel-type plate 10, a counter-plate 11 and a container 1 for receiving a sample, as well as means for obtaining the sample 4 inserted into the container for receiving the sample after the sample was obtained and closing the same in a sealing manner, wherein the means for obtaining the sample 4 comprises a hollow tip and the counter-plate 11 has no through-opening for the mandrel.

DETAILED DESCRIPTION OF THE INVENTION

Figure 1:
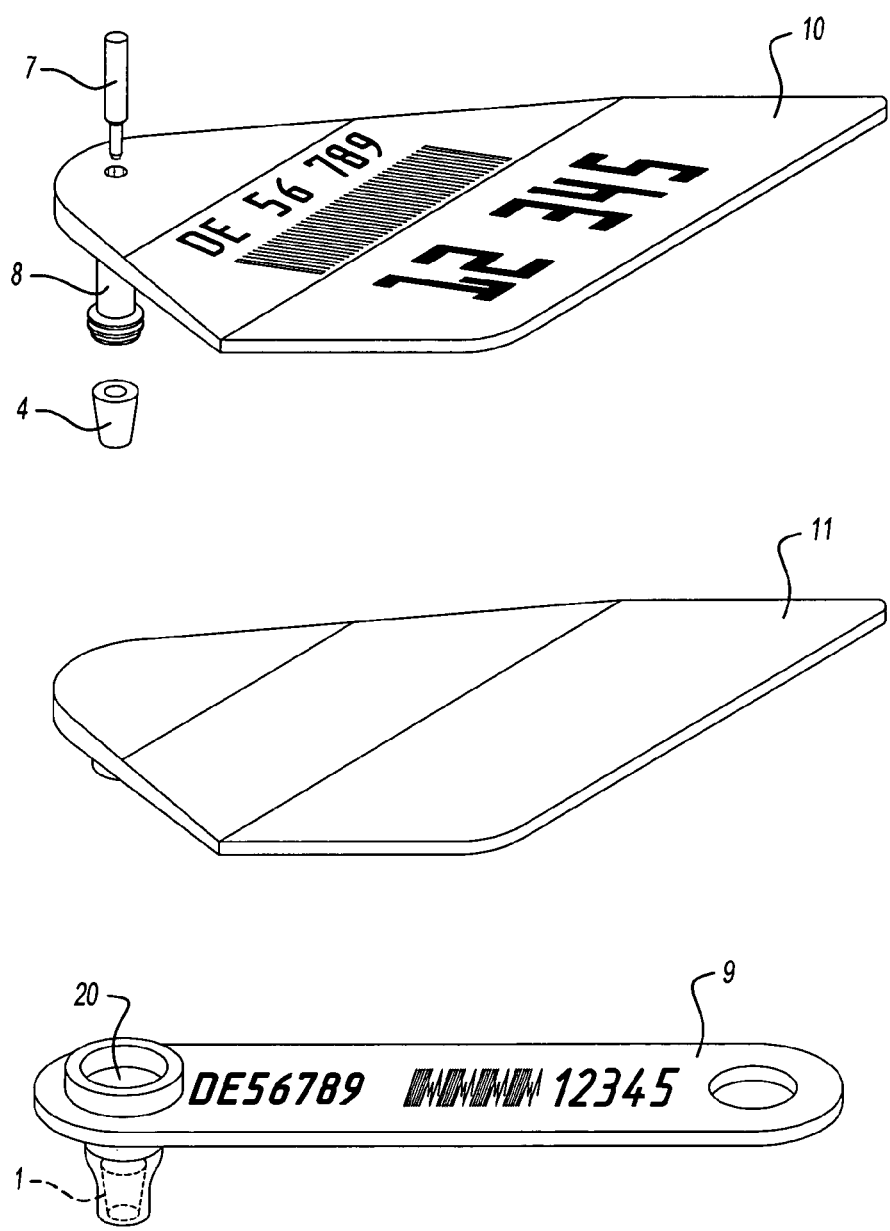
FIG. 1 shows a functional image of ear tag parts, means for obtaining a sample 4 and a container 1 for receiving the sample.

The designations in the figures are:
1 container for receiving a sample
2 bottom part of 1
3 side walls of 1
4 means for obtaining a sample
5 retaining device for 4
6 sample space
7 front end of 4
8 mandrel
9 bracket
10 mandrel-type plate of the ear tag (male part)
11 counter-plate (punching plate) of the ear tag (female part)
12 inner bore of 4 and 8
13 positioning ring of 1
14 positioning ring of 11
15 connecting webs between 1 and 11
16 predetermined breaking point
17 metallic sleeve in the mandrel tip
18 annular groove as predetermined breaking point in 2
19 intermediate bottom in 4
20 retaining shoulder for mandrel basis
21 epidermis—inside of ear
22 corium
23 subcutis
24 ear cartilage
25 subcutis
26 corium
27 epidermis—outside of ear The aforementioned modifications for the construction of ear tags allow to either avoid the disadvantages known in connection with the prior art entirely (during the withdrawal of the sample), or to at least reduce them considerably (during the healing).

In the ear tags according to the invention the tip of the mandrel used for the known ear tags is replaced by a hollow tip having a tip opening whereof the diameter preferably corresponds to essentially the diameter of the mandrel. Said hollow tip is preferably made of a hard material such as metal, which may be provided with a cut edge, or glass, ceramics, a hard plastic material or a similar material, or it comprises an adopted insert from one of said materials. According to a preferred embodiment the cutting edge of the hollow tip has a wavy course, so that the first contact between the edge and the ear occurs punctually at two or more positions. The epidermis is very slightly penetrated at said positions and, as a result of additional pressure and the penetration of the tip, the entire round of the hollow opening is passed into and through the ear. In this case less force is required for the penetration, as the punching process is at least partially replaced by a kind of cutting process.

The shape of a hollow tip moreover allows the insertion and fixation of a marking means, e.g. an electronic chip or the like, which can be identified/recognized from the outside, in the bottom of the hollow tip. During the insertion of the ear tag and the recovery of the tissue sample said marking means/chip is automatically transferred into the container 1 for receiving the sample together with the tissue sample and is suited to mark the sample in the same. The electronic code on the chip in the mandrel tip is identical with the electronic code of the chip fixed or welded on the ear tag. Thus, the sample, the container 1 for receiving said sample as well as the mandrel tip and the ear tag are clearly electronically marked, without requiring the linkage of data, e.g. electronically by means of electronic data processing.

For ensuring that the ear tag and the receiving container remain reliably together after they have been marked with letters, the container 1 for receiving the sample is connected with the counter-plate 11 of the ear tag by means of at least one web 15. Said connection preferably comprises a predetermined breaking point being configured such that, when the container 1 for receiving the sample is separated from the counter-plate 11 of the ear tag, the web remains on the container 1 for receiving the sample and not on the flag 11.

The male flag or mandrel-type plate 10, respectively, and the female flag or counter-plate 1, respectively, may be connected with each other on the lower edge by means of a narrow plastic web, so that the ear tag forms one unit together with the sample container, which is marked with letters in one working cycle and is folded for delivery purposes. Prior to the insertion of the ear tags, both flags may be separated from each other by tearing them off when the ear tag parts are inserted into the tongs.

If the connection between both flags is not removed, the flags 10, 11 of the inserted ear tag remain connected. This entails that, for example when the animals are put out to pasture, wires or cords cannot wind around the ear tags or the mandrel of the ear tags, respectively, as the inserted ear tag constitutes a closed ring. Thus, a frequent cause for the tearing out of ear tags is avoided.

The counter-plate of the ear tag does not comprise an opening for inserting the mandrel and, thus, differs from all known ear tags, all of which are provided with an opening in the counter-plate. For facilitating the attachment of the ear tag, a marking may be provided at the position at which the mandrel 8 is meant to penetrate through the counter-plate 11, whereby said marking allows to find out as to where the mandrel is to encounter and penetrate the female flag. As an example for such markings a cross or a small cavity may be mentioned, whereby said measures likewise facilitate the insertion or passage of the mandrel 8 through the female flag 11.

The container 1 for receiving the sample is preferably sealed in an air-proof or water-proof manner by means of a foil welded on by ultrasound or pasted onto the same, or by means of another device.

Moreover, the female flag 11 and the container 1 for receiving the sample are fixed in a folded state by means of two adjusted positioning rings 13, 14 such that the portion above the container 1 for receiving the sample is hermetically sealed. The rings 13, 14 are preferably constructed such that they taper from the upper edge towards the basis. This ensures that the rings 13, 14 are engaged with each other when the female flag 11 and the container 1 for receiving the sample are folded and are adjacent to each other so closely, that they can be closed in an air-proof and water-proof manner. The positioning rings 13, 14 moreover guarantee that the container 1 for receiving the sample is arranged exactly in the right position of the female flag 11, so that the tip of the mandrel 4, 8 is pressed exactly into the receiving container when the ear tag is inserted.

When the ear tag is attached, said portion is opened with the hollow tip of the mandrel 4 only when the female flag 11 is punctured. At the same time the possibly provided covering membrane/foil of the container 1 for receiving the sample is punctured, and the two spaces are thus connected for a short period until the means 4 for obtaining the sample has completely been inserted into the container 1 for receiving the sample and seals the same.

In principle, material may be stored in the space formed by the female flag 11 and the container 1 for receiving the sample, which is to come into contact with the sample during the withdrawal of the sample. Thus, it is possible to utilize two spaces separated from each other for loading them with components, which are to be brought into contact and, for example, activated only when the sample is punched. It is moreover possible to apply artificial oligonucleotides constituting a DNA coding of the ear tag number onto the membrane sealing the container 1 for receiving the sample. As this space is protected against influences from the outside, the oligonucleotides remain stable until the ear tag is used. When the sample is punched, said oligonucleotides are automatically co-transported into the sample chamber.

Figure 2:
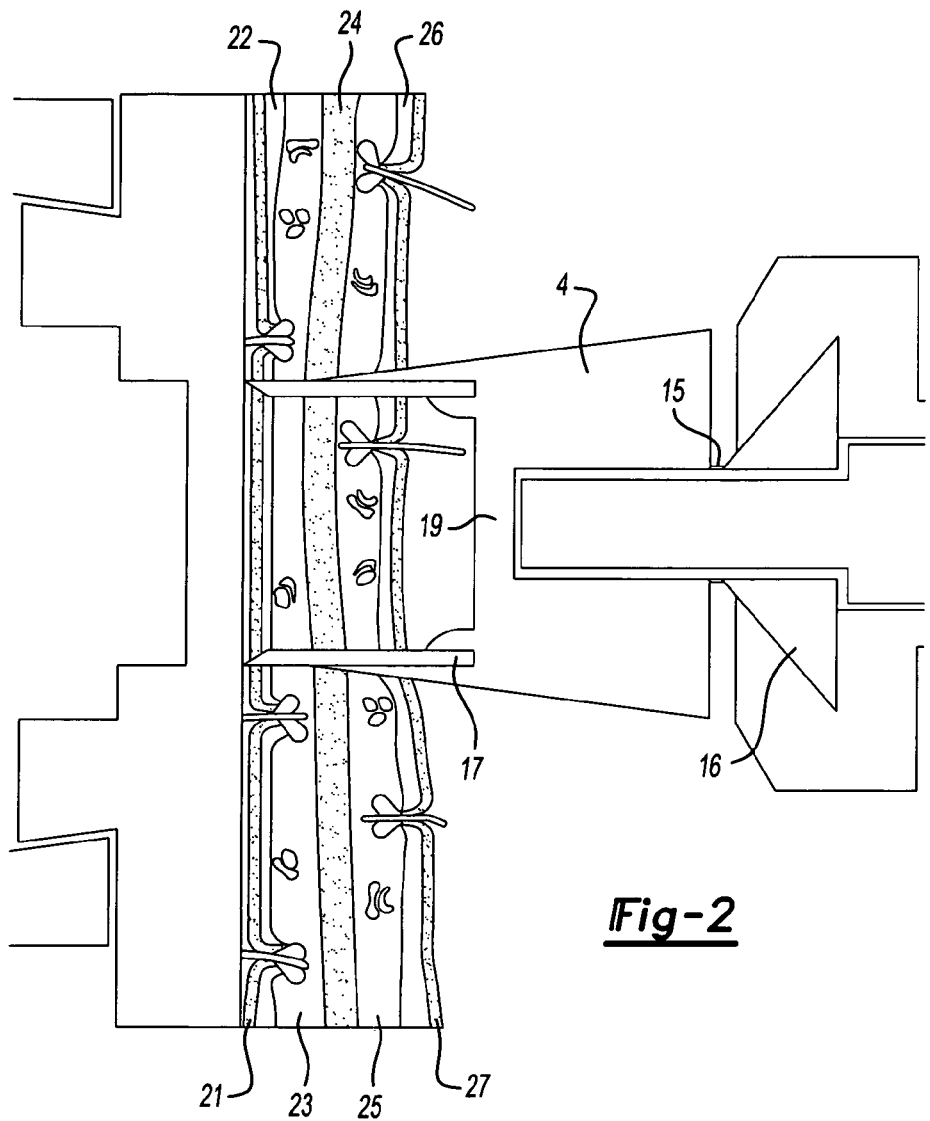
FIG. 2 schematically shows a punching procedure when the ear tag is inserted.
Figure 3:
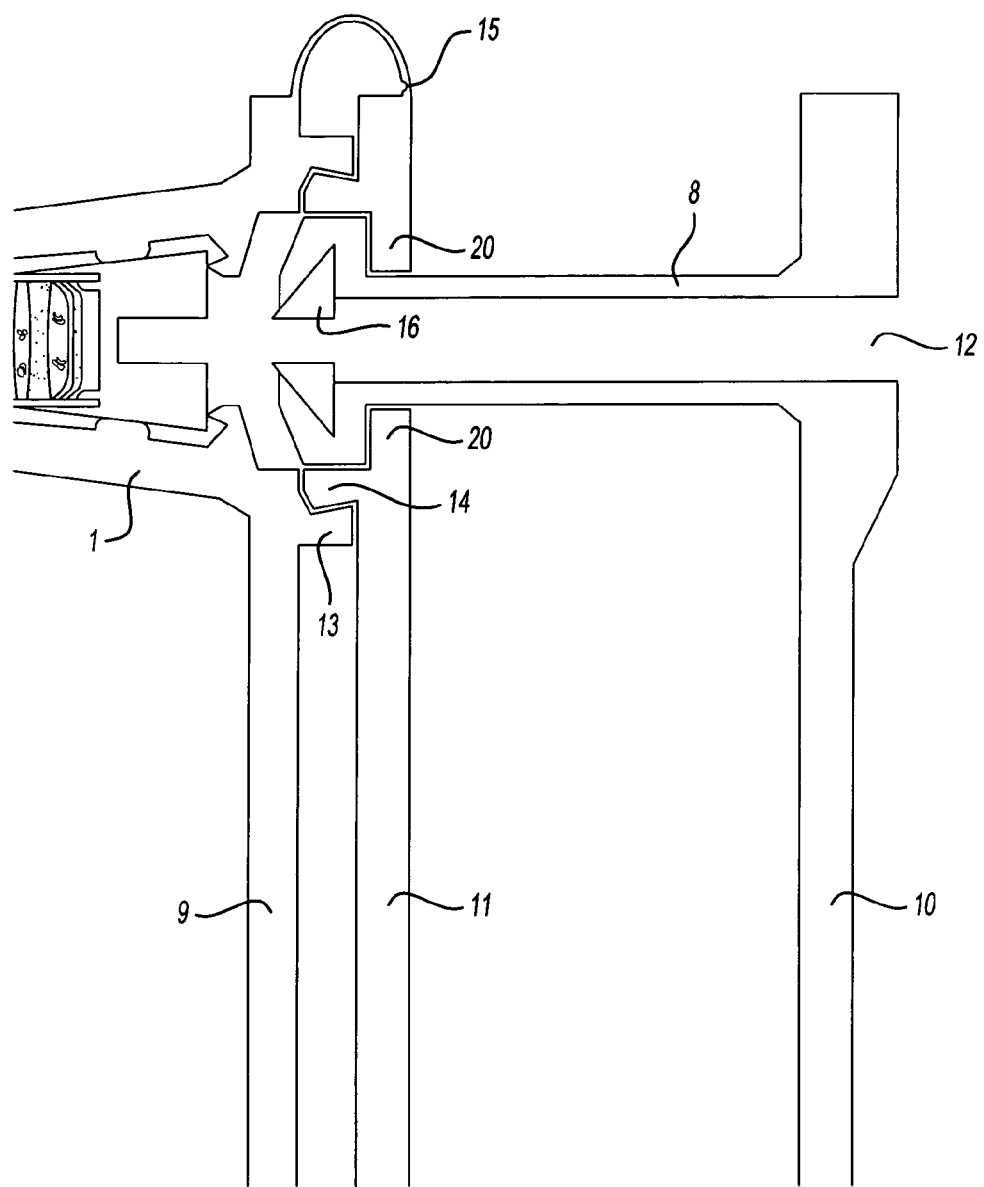
FIG. 3 shows a cross-sectional view of ear tag parts, the container 1 for receiving the sample and means 4 for obtaining the sample directly after the ear tag was closed and the sample was obtained.
Figure 4:
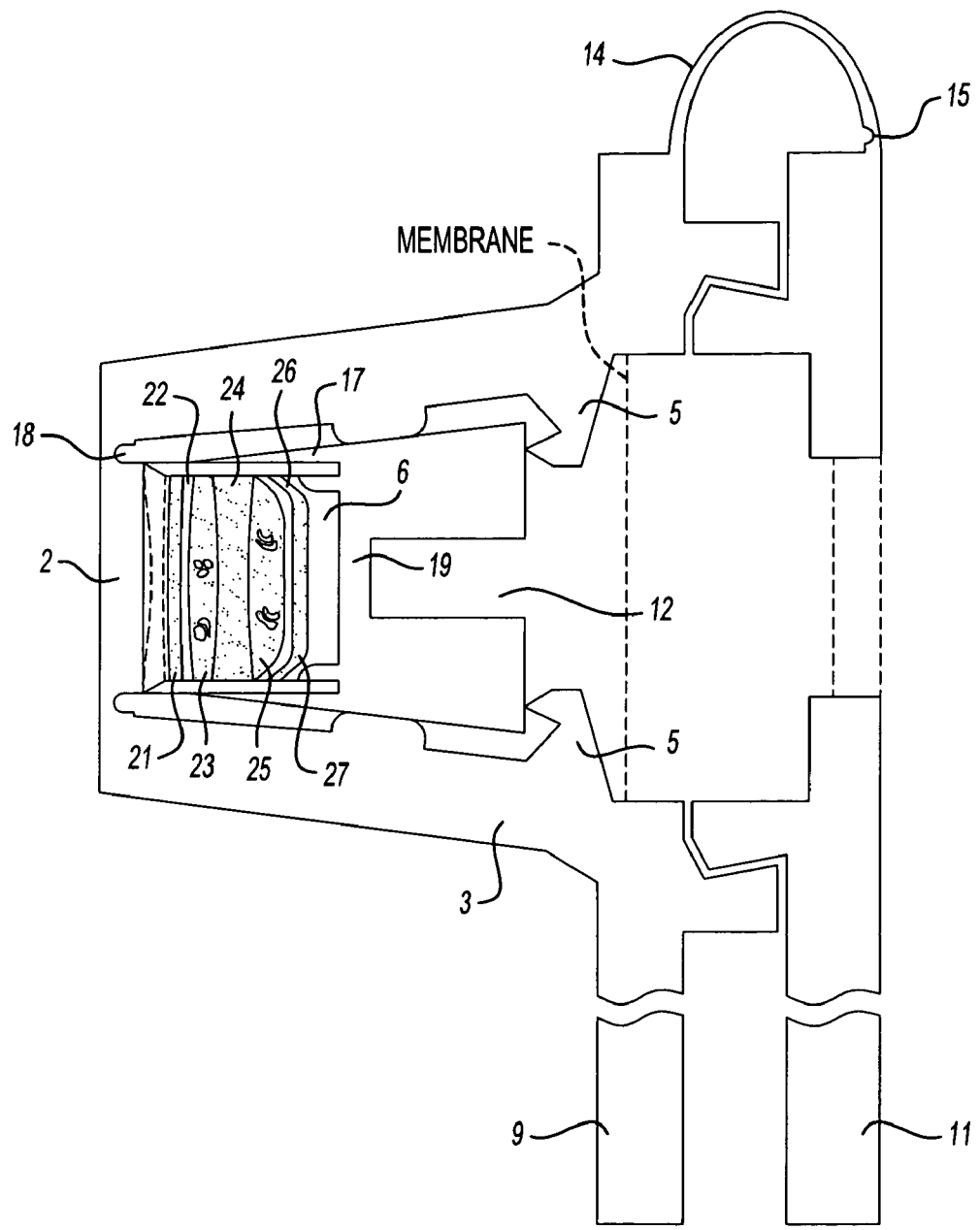
FIG. 4 shows an enlarged view of FIG. 3 with the container 1 for receiving the sample and the means 4 for obtaining the sample with a punched and packed sample.

When the ear tag is attached, the entire ear is punctured by pressing the edge of the hollow tip against the plastic material of the counter-plate (see FIG. 2), whereby the punched tissue is placed in the hollow up. Subsequently the mandrel 4, 8 penetrates the female flag 11 at the position provided for said purpose, wherein a plastic ring is punched out of the flag or a part of the point of penetration is ripped up, so that the mandrel 4 can slip through the so formed opening. In case of said ear tags, too, the mandrel 4 closes the ear tag and fixes the two ear tag parts 10, 11 with each other.

For increasing the punching effect, the portion of the female flag 11, which is encountered by the hollow tip of mandrel 4, may be slightly oppositely arched towards said tip or may comprise a small groove, into which the punching head penetrates when being pushed through. Moreover, a metallic ring can be inserted/cast into the female flag 11, which constitutes a counter-bezel for the metallic sleeve of the mandrel so that, when the ear tag is closed, a process takes place, during which two metallic bezels are moved against each other and the tissue placed therebetween is exactly cut on the sharp edges.

In fact, a precisely round-shaped hole can usually be punched out of the ear by means of the ear tag according to the invention. According to tests with pieces of tissue, which were punched out by means of the inventive ear tags, said pieces of tissue—when inserting the ear tag from the inside of the ear towards the outside—have the following composition.

1. epidermins—inside of ear
2. corium
3. subcutis
4. ear cartilage
5. subcutis
6. corium
7. epidermis—outside of ear This structure of the punched out piece of tissue clearly shows that, when the modified ear tag is inserted, the entire ear was punched through and material was obtained from all existing tissue layers.

Proof of the actual complete punching of the ear could also be achieved by that ears from slaughtered animals showed precise circular holes having the diameter of the used hollow tip, after the insertion and the subsequent removal of the ear tag. Thus, when the ear tag was inserted, a disc of ear tissue had precisely been punched out and removed from the ear, so that the edges of the hole could not be placed side by side once the ear tag was removed, as the punched out round piece of tissue was missing.

Even though the use of conventional ear tags likewise resulted in an opening in the ear after the freshly inserted ear tag was removed, said opening was not a round hole, but a slot-shaped tear, the edges of which could again be placed side by side after the ear tag was removed, since apparently no significant loss of substance had occurred.

The healing of the ear tag into the ear can additionally be improved in that it is achieved, by applying bacteriostatically or bacteriocidally working substances on the mandrel of the ear tag, that the same, after the insertion of the ear tag, prevents/suppresses the formation of a bacterial inflammation on the punched edges. As the mandrel can move freely in the ear hole, the healing tendency is not impeded by chafing and rubbing effects and, moreover, no secretion is congested. The proceeding processes come very close to those of a "healing of a wound by first intention" without complications.

The herein described modified ear tags can, in principle, be inserted with all existing conventional ear tag tongs from different manufacturers. In case of need, merely smaller technical modifications for the accommodation of the containers 1 for receiving the sample are required.

The hollow tip of the mandrel is formed such that its basis, which is connected with the actual mandrel via a predetermined breaking point/detachment point, closes the container 1 for receiving the sample in a sealing manner. At the same time, the intermediate bottom can be designed such that it is thin enough to allow the breaking through thereof in the laboratory when recovering the sample from the receiving container. The recovery of the sample from the receiving container may take place such that, in a first step, the entire head of the mandrel located with the sample in the receiving container is pressed by a pin accommodated in the inner bore of the mandrel head through the bottom of the receiving container by some millimeters. The plastic bottom of the receiving container thereby already gets torn, but the sample is not yet pressed out as the intermediate bottom still in intact.

The portion of mandrel head located outside the sleeve is now fixed or, respectively, retained by an annular device. By additional pressure exerted by the pin located in the inner bore on the intermediate bottom said intermediate bottom is broken out, whereby the sample is transported into a receptacle located underneath the receiving container. Materials (enzyme solutions) for the digestion of the tissue sample may already be provided in said receptacle. After the digestion of the tissue sample an aliquot of said solution is taken up by a hollow needle or pipette tip pushed through the inner bore of the mandrel head and is transferred, for example, into a 96-Well plate. In another pipetting step into the receptacle of the sample container 1 the effect of the eye solution may be stopped by certain substances pipetted into the same, and additional substances preparing the DNA for the storage may be added.

The rear opening of the container 1 for receiving the sample may either be closed by welding a plastic foil onto the same, or it may be covered by a closely sealing cap. The container 1 for receiving the sample, which is provided with the identification number of the animal, and which may also contain an electronic chip and artificial oligonucleotides codifying the number, may be stored as a reserve sample or as part of a genomic DNA bank. This allows the doubtless and error-free access to the tissue/DNA samples of all previously marked animals even after a storage time of several years.

EXAMPLE 1

Recovery of DNA Samples From Lambs

During the first days after the birth of 40 milk sheep lambs samples were obtained from the ears by means of ear tags. All 40 ear tags, which comprised a closed female flag and a mandrel hollow tip diameter of 3.2 mm, contained complete pieces of tissue with skin from the inside and the outside as well as cartilage of the ear in the receiving container. During the isolation of DNA from said pieces of tissue with a kit from Machery & Nagel, or by means of the column method by Mira, more than 20 µg high-molecular DNA were isolated.

EXAMPLE 2

Recovery of DNA Samples From Adult Cows

By means of modified ear tags, which had a hollow tip diameter of 5 mm in correspondence with the mandrel diameter, tissue samples were withdrawn form the ears of slaughtered adult cows (older than 18 months). In all cases a complete tissue sample (2× skin and subcutis and 1× cartilage) could be withdrawn from the container 1 for receiving the sample. After the insertion the ear tags were freely movable in the punched out hole. In all cases the amount of DNA isolated from said tissues was more than 100 µg of high-molecular DNA. When the ear tags were removed, it could be found that in all cases a round hole (Ø 5 mm) had been punched out of the ear.

The invention claimed is:

1. An ear tag comprising;
   a mandrel plate (10) having a mandrel (8),
   a counter-plate (11) having a planar surface for receiving the mandrel (8) wherein the planar surface lacks an opening for the mandrel (8) such that the mandrel (8) penetrates the planar surface during use,
   a container (1) for receiving a sample, and
   a hollow tip (4) detachably engaged with said mandrel (8) and having a cut edge for obtaining the sample and sealing the container (1) when the detachable hollow tip (4) is inserted into the container (1) after the sample is obtained.

2. An ear tag according to claim 1, wherein the container (1) for receiving the sample is sealed in an air-tight and water-proof manner.

3. An ear tag according to claim 2, including a membrane onto which oligonucleotides are applied for marking the obtained sample.

4. An ear tag comprising;
   a mandrel plate (10) having a mandrel (8),
   a counter-plate (11) having a planar surface for receiving the mandrel (8) wherein the planar surface lacks an opening for the mandrel (8) such that the mandrel (8) penetrates the planar surface during use,
   a container (1) for receiving a sample, and a hollow tip (4) detachably engaged with said mandrel (8) and having a cut edge for obtaining the sample and sealing the container (1) when the detachable hollow tip (4) is inserted into the container (1) after the sample is obtained,
   wherein the detachable hollow tip (4) has a cutting edge with at least one undulation.

* * * * *